US00PP08696P

United States Patent [19]

de Jong

[11] Patent Number: Plant 8,696

[45] Date of Patent: Apr. 19, 1994

[54] ALSTROEMERIA NAMED MONTREUX

[75] Inventor: Cornelis T. J. de Jong, Roelofarendsveen, Netherlands

[73] Assignee: Agroplant-Select B.V., De Kwakel, Netherlands

[21] Appl. No.: 36,653

[22] Filed: Mar. 24, 1993

[51] Int. Cl.[5] ..... A01H 5/00

[52] U.S. Cl. ..... Plt./87.1

[58] Field of Search ..... Plt. 87.1

[56] References Cited

U.S. PATENT DOCUMENTS

PP. 6866 6/1989 Van Beldeven ..... Plt. 87.1

*Primary Examiner*—James R. Feyrer

[57] ABSTRACT

A new and distinct cultivar of Alstroemeria plant named Montreux, characterized by its distinctive predominantly purple flower with outer petals having green tips, moderate red-brown spotting concentrated in area around the green tips, moderate dark purple streaking; the top inner petals are lighter purple at the base, purple at the apex and have a creamy-yellowish band; patterns of numerous dark purple elongated stripes, on the top two inner petals; and, with the bottom inner petal being purple with dark purple streaking.

1 Drawing Sheet

BACKGROUND OF THE INVENTION

The present invention comprises a new and distinct cultivar of Alstroemeria plant referred to by the cultivar name Montreux. Montreux was originated from a hybridization program in Roelofarendsveen, The Netherlands in 1985. The female parent was an unnamed hybrid from our own breeding. The male parent also was an unnamed hybrid from our own breeding. Each of the parent plants were proprietary, and have not been released or marketed, and are maintained strictly for use in the breeding program. Montreux was discovered and selected as one flowering plant within the progeny of the stated parentage by me on Jul. 21, 1985 in a controlled environment in Roelofarendsveen, The Netherlands. The first asexual reproduction of Montreux was accomplished when vegative cuttings were taken from initial selection on Nov. 6, 1985 in a controlled environment in Roelofarendsveen in The Netherlands. Horticultural examination of selected units initiated in November 1985 has demonstrated that the combination of characteristics as herein disclosed for Montreux are firmly fixed and retained through generations of asexual reproduction. The following observations, measurements and comparisons describe plants grown in Roelofarendsveen, The Netherlands under greenhouse conditions which approximate those generally used in commercial practice. The following traits have been repeatedly observed and are determined to be basic characteristics of Montreux, which in combination distinguish this Alstroemeria from its parents and all other varieties of which I am aware:

1. The outer petals have a distinctive purple color, green tips with moderate dark purple streaking and red-brown spotting concentrated in area around the green tips.
2. The two top inner petals have a light purple-pink color at the base, a creamy-yellow band at the center and have outer ends that are purple similar to the purple color of the outer petals.
3. The inner petals have many dark purple streaks which increase in length and width from the attachment point to the apex of the petals.

BRIEF DESCRIPTION OF THE FIGURE OF THE DRAWING

The accompanying photographic drawing of a closeup of the flower in bloom and buds shows typical inflorescence and foliage characteristics of Montreux nearly as true as possible with illustrations of this type. In the following description, color references are made to The Royal Horticultural Society Color Chart (RHS). The color values were determined in the afternoon in May 1986 at Roelofarendsveen, The Netherlands.

BOTANICAL DESCRIPTION OF THE PLANT

Botanical: Alstroemeria cv Montreux.
Commercial: Alstroemeria.

PLANT

A. General appearance:

*Form.*—Typical of genus, but shorter and more compact than usual, upright, spreading by rhizomes

*Height.*—Varies with light intensity and season. Measured from the surface of the soil to the highest flowers: Summer: about 120–150 cm. Winter: about 130–160 cm. (If grown as a bedding plant outside the plant will have an average height of about 40 cm during the summer and about 50 cm during the winter).

*Growth.*—Upright bush forming, spreading by rhizomes; vigor is average.

This plant is used for cut flower production

B. Foliage:

*Quantity.*—Medium.

*Stems.*—Mature: about 50–70 yearly.

*Number of leaves.*—Varying from season to season through the year.

*Internode.*—Length: about 10 cm; varies with light intensity and season.

*Size of leaf.*—Length: Long, about 10 cm. Width: Broad, aboutt 4 cm.

*Shape of leaf.*—Elliptical.

*Color of leaf.*—Typical for members of the genus. upper side: dark green. under side: dark green.

*Texture.*—Smooth.

C. Rhizomes:

*Color.*—White.

*Size.*—Average.

INFLORESCENCE

A. Bud:

*Form.*—Medium to large broadly elliptical.

*Size.*—Diameter: About 2.5 cm just prior to opening. Length: About 4 cm.

*Receptacle.*—Color: RHS 71C-D.

B. Flower:

*Size.*—Width: about 8 cm. Depth: about 4 cm.

*Borne.*—Umbel of about 5 branches of substantially uniform length; each bearing about 3 or more buds on short peduncles.

*Blooming habit.*—When grown under controlled conditions: continuous whole year round. The plant would bloom freely when grown as a bedding plant. The plant produces blind stems in the fall and winter.

*Shape.*—Cupped to funnel-like.

*Outer petals.*—Shape: Lobed. Size: Length: about 4 cm; width: about 2 cm. Color: Near to RHS 71 C-D, slightly lighter towards the base with green tips; and, fine brownish-red spots in the area around the green tips, and few dark purple streaks. Margins: Irregular indentations.

*Reverse side.*—Near to RHS 71 C-D

*Inner petals.*—Shape: Lanceolate. Size: Both upper and lower: Length: about 3 cm; Width: about 1-1.5 cm. Color: upper inner petals: Creamy band near to RHS 155-B with the base RHS 73-C/75-C, and upper portions near to 71 C-D; and, dark purple streaking increasing in length and width from the attachment point to the apex. lower inner petal: predominantly purple near RHS 71C-D with dark purple streaking. Reverse side: Purple near to 71 C-D. Margins: irregular undulations.

*Texture.*—Smooth.

*Peduncle.*—Color: Medium green with light anthocyanin. Length: Average about 10 cm.

*Fragrance.*—None.

*Lasting quality.*—Approximately 14 days. Petals hang on and dry.

Flower production of Montreux is about 20% above average production of genus.

C. Reproductive organs:

*Size.*—Typical for genus.

*Stamens.*—Number: 6.

*Anthers.*—Color: Before the pollen is released: olive green. When pollen is released: dark purple.

*Pollen.*—Color: Purple.

*Filaments.*—Color: Light purple.

*Pistils.*—Color: Anthocyanin. Number: 1.

*Stigma.*—Color: Purplish-pink.

*Fertility.*—Easy.

Zelpado differs from Montreux by having longer stems, more, longer and smaller foliage, and a different shape of flower.

I claim:

1. A new and distinct cultivar of Alstroemeria named Montreux, as illustrated and described herein, characterized by its distinctive purple outer petals with moderate dark purple streaking and fine red-brown spotting in area around the green tips, and distinguished by the creamy-yellow and purple color with darker purple streaking of the two top inner petals.

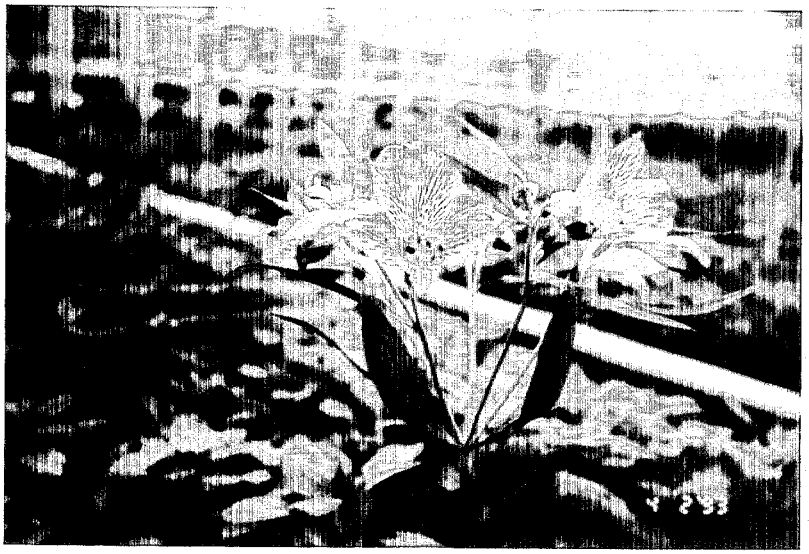

* * * * *